United States Patent [19]

Stephan et al.

[11] Patent Number: 4,654,441
[45] Date of Patent: * Mar. 31, 1987

[54] BIURET PRODUCTION BY CONTROLLED PYROLYSIS OF UREA

[75] Inventors: Kurt F. Stephan, Ephrata; John T. Stephan, Longview; Steven R. Klein, Ephrata, all of Wash.

[73] Assignee: Moorman Manufacturing Company, Quincey, Ill.

[ * ] Notice: The portion of the term of this patent subsequent to Sep. 10, 20002, has been disclaimed.

[21] Appl. No.: 265,550

[22] Filed: May 20, 1981

Related U.S. Application Data

[63] Continuation-in-part of Ser. No. 178,132, Aug. 15, 1980, abandoned.

[51] Int. Cl.⁴ .............................................. C07C 127/24
[52] U.S. Cl. .......................................................... 564/38
[58] Field of Search ........................................... 564/38

[56] References Cited

U.S. PATENT DOCUMENTS

| | | | |
|---|---|---|---|
| 2,145,392 | 1/1939 | Harmon | 564/38 |
| 2,370,065 | 2/1945 | Olin | 564/38 |
| 2,524,049 | 10/1950 | Garbo | 564/38 |
| 2,861,886 | 11/1958 | Colby | 564/38 X |
| 3,057,918 | 10/1962 | Formaini et al. | 564/38 |
| 3,150,177 | 9/1964 | Kluge | 564/38 |
| 3,453,098 | 7/1969 | Kamlet | 564/38 X |
| 3,928,438 | 12/1975 | Beale et al. | 564/38 |
| 3,935,260 | 1/1976 | Schlosser | 564/38 |
| 3,946,073 | 3/1976 | Cook | 564/38 |
| 4,055,598 | 10/1977 | Lee | 564/38 |

FOREIGN PATENT DOCUMENTS

| | | | |
|---|---|---|---|
| 1068693 | 11/1959 | Fed. Rep. of Germany | 564/38 |
| 95513 | 9/1960 | Netherlands | 564/38 |
| 830114 | 3/1960 | United Kingdom | 564/38 |

*Primary Examiner*—Charles F. Warren
*Attorney, Agent, or Firm*—Graybeal & Cullom

[57] ABSTRACT

Process for the production of technical grade biuret, readily in a form suitable for use as animal feed, by the controlled pyrolysis of urea in two stages, the first stage involving the partial pyrolysis of urea at a temperature above the melting point of urea to produce a first stage intermediate reaction product containing from about 20% to about 60% urea, and not more than about 25% cyanuric acid by weight, such reaction product being then cooled and comminuted, the comminuted product then being subjected, in solid form and in the absence of a liquid carrier, to a temperature at or slightly below the softening point of the solid particulate (suitable at a temperature of from about 100° C. to about 140° C.) with forced air circulation through the comminuted product for a sufficient time to lower its urea content by partial sublimation of the urea and partial further reaction thereof to biuret with only minimal further conversion of urea to cyanuric acid. Crystallization and cooling of the molten intermediate product resulting from the first stage of pyrolyzation is advantageously accelerated by addition thereof of a powdered seed material, preferably including powdered feed grade biuret from a previous run, which additive serves to also increase the melting point of the product and thus increase the temperature at which it may be heated during the solid state pyrolyzation.

17 Claims, No Drawings

BIURET PRODUCTION BY CONTROLLED PYROLYSIS OF UREA

CROSS REFERENCE TO RELATED APPLICATION

This application is a continuation-in-part of application Ser. No. 178,132, entitled Production of Biuret by the Controlled Pyrolysis of Urea, filed Aug. 15, 1980, and now abandoned.

TECHNICAL FIELD

This invention relates to a process for the production of animal feed grade biuret and more specifically to the pyrolyzation of urea and its reaction products in two stages, the first stage of the reaction proceeding with the urea in molten form and resulting in a reaction product which comprises about 20% to 60% unreacted urea, and the second stage of which involves further pyrolyzation of the product in dry, particulate, solid form to reduce the urea content and increase the biuret content without substantial further increase in cyanuric acid content.

BACKGROUND ART

As is well-known, an animal feed shortage exists worldwide. Feed which has a high protein analysis is in particularly short supply. Historically, cattle have been fed with grass hay, and the raising of such hay for winter feeding is a well-established traditional procedure.

Grass hay contains up to 20% protein if harvested in the early summer. However, there is a decline in the protein content as the summer progresses, making later cuttings of hay less valuable for cattle growth.

After July 1st, the intermountain natural grazing area of the United States produces a natural hay which has a protein content below 10% on the dry basis. When hay has a protein content below this level, the ruminant animal eating such hay does not gain weight at a satisfactory rate.

Consequently a great deal of research effort has been devoted to the establishment of diets and feeding schedules for ruminant animals which will maximize the profit to be realized in raising such animals. It was discovered early that protein-rich leguminous hay produced not only better quality meat, but also more pounds of meat per acre. This discovery has led to the use of protein-rich agricultural by-products as additives to hay to enrich the diet of the animals when hay of low protein analysis is fed.

Such agricultural products as cottonseed meal, soybean meal, peanut meal, flax seed meal, etc. are widely used along with the hay in order to upgrade the average protein analysis of the resulting feed mixture. At the present time, escalating costs of farming and ranching make it imperative that any mixed feed fed to the cattle be of lowest cost and the search for readily available, economic feeding additives of consistent quality continues.

It was discovered many years ago that it is not necessary to feed protein per se to ruminant animals in order to increase the protein content of the animal. The animal itself has the ability to convert non-protein materials into protein.

Thus, it was discovered about 1920 that inorganic nitrogen in the form of ammonium salts could be used to supplant protein in part of the diet of a ruminant animal. The ammonia content of the ammonium salts is converted by the animal into muscle tissue. Ruminants have multiple stomachs and ammonium salts release their ammonia content in the rumen, where it is converted into protein by the bacteria occurring naturally there. When the bacteria-produced protein passes into another stomach of the ruminant, it is digested just like any other feed protein.

Ammonia and ammonium salts are an inexpensive source of non-protein nitrogen utilizable in this manner. Unfortunately, there is a limit to the amount of ammonia which can be included in the diet of the animal without causing the occurrence of adverse reactions. These adverse reactions are believed to be caused by the absorption of unconverted ammonia in the digestive system of the animal.

Such absorption results in ammonolysis, a condition wherein the ammonia in the digestive system of the animal causes toxic effects and possible death. Consequently the amount of free ammonia which can be tolerated by an animal is very small. The use of ammonium salts as a source of non-protein nitrogen in mixed feeds, therefore, has not been a commercial success.

Urea is used widely today in limited amount as a non-protein nitrogen additive to mixed feeds for ruminants. The economic incentive to use urea as a source of non-protein nitrogen is great. It has its basis in the fact that urea is 46% nitrogen by weight, whereas hay analyzing 10% protein is only 1.6% nitrogen. In other words, the addition of 20 pounds of urea (1% of the dry weight) to a ton of 10% protein hay produces 2,020 pounds of hay having a protein equivalent of approximately 13%. It would require the addition of only 74.77 pounds of urea to bring the protein equivalent of the hay up to 20%.

With hay having a current market value of $75.00 per ton and urea of $165.00 per ton, the economic advantage of adding urea to hay is obvious.

However, the use of urea is generally restricted to between ½% and 1% of the dry weight of the mixed feed because of the toxicity which develops when urea is overfed. This toxicity is due to the hydrolysis of the urea by the enzyme urease generally present in the stomach of the ruminant animal. When urea is hydrolyzed by urease, it gives off free ammonia and the toxicity which results in the animal is in reality the earlier recognized toxicity due to free ammonia.

Because of the restriction due to ammonolysis on the use of urea, the search continued for an alternate hay additive. This search has led to the discovery that biuret, a compound which can be made from urea, can also be used by ruminant animals in the synthesis of protein.

Biuret is not readily hydrolyzed by the enzyme urease and consequently can be included in the diet of ruminants without danger of toxicity. Biuret which is unused as a symbiotic feed for the ruminant passes through the digestive tract unchanged. This makes it virtually impossible for toxic symptoms to develop when feeding biuret as a diet supplement. U.S. Pat. Nos. 2,768,895 and 2,861,886, for example, describe the use of biuret in animal feeds.

It is not necessary to use pure biuret in the supplementation of animal feeds. A technical grade product analyzing as little as 55% biuret may be used satisfactorily. The commercial standard for feed-grade biuret adopted by the U.S. Food and Drug Administration is a mixture having a minimum analysis for biuret of 55%, a maximum of 15% urea, and not more than 30% of the group consisting of cyanuric acid and other urea derivatives, by weight.

These materials result from the conversion of urea to biuret by heating the urea to a temperature above its melting point. Thereupon ammonia gas is evolved and there results a reaction mixture comprising in varying amounts the following products:
Unreacted urea
Ammonium cyanate
Cyanuric acid
Biuret
Triuret
Tetrauret
Higher homologs In carrying out this pyrolytic reaction, it is not possible to achieve a yield of biuret over about 60% when operating at a temperature above the melting point of urea and at any partial pressure between 10 and 60 mm with a reaction time of from 30 minutes to 16 hours. The longer the reaction time, the greater the yield of cyanuric acid, which after a reaction time of about 12 hours is generated in ever-increasing amounts at the expense of the desired biuret product.

The production of biuret by pyrolysis of urea under elevated temperatures is well-known and a considerable art has developed as shown by the following patents showing various methods of biuret manufacture:
U.S. Pat. No. 2,145,392 to Harmon
U.S. Pat. No. 2,370,065 to Olin
U.S. Pat. No. 2,524,049 to Garbo
U.S. Pat. No. 2,768,895 to Kamlet
U.S. Pat. No. 2,861,886 to Colby
U.S. Pat. No. 3,057,918 to Formaini
U.S. Pat. No. 4,055,598 to Lee All of these patented processes involve the pyrolysis of urea in the molten state or liquid phase, in a single step, which may be under vacuum, to facilitate the removal of by-product ammonia which occurs according to the following chemistry:

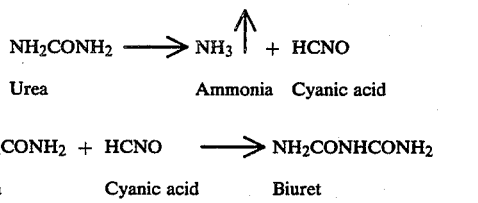

NH$_2$CONH$_2$ + HCNO ⟶ NH$_2$CONHCONH$_2$

Urea     Cyanic acid     Biuret

Biuret and cyanic acid also may react to form cyanuric acid as follows:

NH$_2$CONHCONH$_2$ + HCNO ⟶

Biuret     Cyanic acid

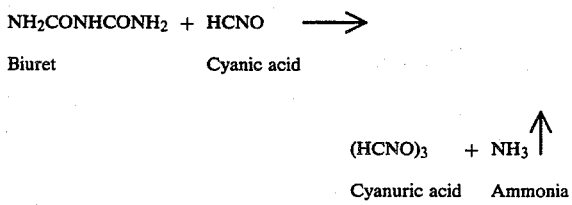

The formation of cyanuric acid is enhanced by elevated temperatures and reduced pressures and retarded by lower reaction temperatures.

Heretofore, purification and concentration of the biuret product has been necessary in order to produce a feed-grade biuret meeting Food and Drug Administration requirements.

This is difficult because cyanuric acid and urea cannot be separated with ease from biuret. Ordinary routines of fractional crystallization do not lead to the production of a pure, crystalline, dry biuret product. They lead rather to the formation of a wet, sticky, clay-like filter cake which contains urea in various amounts.

Also if an appreciable amount of cyanuric acid is present, the reaction mixture is viscous and sticks to the reaction and refining vessels, making it hard to handle. In addition, the cyanuric acid tends to combine with the unreacted urea compound of the reaction mixture so that it becomes virtually impossible to separate the urea by filtration, as is normally required to produce the FDA approved low-urea biuret product.

The precise mechanism by which this occurs is not known. However, urea may form an insoluble complex with cyanuric acid in the nature of a secondary valence compound. Alternatively, the urea may simply be strongly occluded by any cyanuric acid present so that in the mixed precipitate of urea, biuret, biuret homologs, and cyanuric acid, the urea is not readily removed by washing with an aqueous solvent for urea. Where a pyrolyzed urea product contains cyanuric acid in excess of 10%, and unreacted urea in excess of 35%, it is not practical to lower the urea analysis to below 15%, even by multiple recrystallizations.

The disclosure of Lee U.S. Pat. No. 4,005,598 includes a good summarization of various prior art processes for pyrolyzing urea to produce reaction products which are principally biuret. The contribution to the art offered by the Lee patent disclosure is that of a process for producing biuret wherein the extent of pyrolytic conversion of urea to biuret is increased, with less than normal amounts of cyanuric acid, triuret and other biuret homolog products being formed, the reaction involving a starting material made up of a low urea, high biuret seed material mixed with a high urea, low biuret feedstock material, which mixture has a total urea content not exceeding 20% by weight, such mixture being heated to a range of from about 100° C. to about 150° C. and preferably from about 115° C. to about 125° C. while dispersed as a slurry in an alkane series hydrocarbon carrier having from 8 to 12 carbon atoms and a boiling point at or above the reaction temperature. In the Lee process, heating of the mixture of low urea seed material and high urea feedstock material proceeds with the mixture in slurry form in the liquid hydrocarbon carrier, with by-product ammonia being removed by evolution of hydrocarbon carrier vapor. This process, although assertedly achieving the objective of permitting the reaction to proceed at relatively low temperature in order to minimize the formation of cyanuric acid and other undesired auto-condensation products, has manifest practical disadvantages in that it requires an essentially liquid phase reaction environment and the toleration of potentially dangerous reaction conditions since the reaction is carried out in the presence of a heated liquid hydrocarbon carrier which inherently presents an explosion or fire hazard.

The Lee process is severely limited in production capacity in that the urea content of the reaction mass is limited to a maximum of 20%. This limitation in the Lee process is dictated by the fact that the Lee reaction product will gum up and not remain a slurry in the liquid medium and in the processing equipment if the urea content exceeds 20%. In contrast, applicant's dry, solid state pyrolyzation process is operable with up to about 60% urea content by weight in the heated reaction mass, which correspondingly increases production capacity insofar as the amount of urea which can be converted to a reaction product suitable for use as feed grade biuret in a given amount of time.

A further disadvantage of the Lee process is that its end product is oil contaminated in the sense of the product retaining some residual alkane hydrocarbon, which detracts from its palatability when used as animal feed. There is also the possibility that residual pyrolyzed hydrocarbon may render the product unsuitable for animal consumption and indirectly human consumption in view of possible carcinogenic risk. Furthermore, a residual oil content in the end product in this type of process may interfere or complicate use of the product or portions thereof in water solution. As a related consideration, the use of an oily, hydrophilic carrier as the reaction medium can complicate evolved ammonia by-product recovery in aqueous solution since the by-product is then recovered in what amounts to an oil-in-water emulsion.

DISCLOSURE OF INVENTION

According to the present invention, partially pyrolyzed urea containing not over 25% cyanuric acid and more than 20% urea by weight may be converted to animal feed grade biuret by subjecting the partially pyrolyzed urea feedstock in particulate form to a mild heat treatment in the substantially solid state with forced air flow through the particulate reaction mass. A product results having a high concentration of biuret and a product with a minimum of 55% biuret, a maximum of 15% urea, and a maximum of 30% cyanuric acid and similar urea pyrolysis by-products is easily produced. Such product is hydrocarbon-free and eminently suitable as a feed additive for cattle and needs no additional separation step to remove excess urea and cyanuric acid.

In carrying out this invention, a feedstock consisting of partially pyrolyzed urea in dry particulate form and containing not over about 25% cyanuric acid which is treated in an oven with forced air recirculation at a temperature at or slightly below the softening point of particles, e.g. at a temperature between about 100° C. and about 140° C., and preferably between 115° C. and 125° C. for a period of time of generally between about 15 hours to about 200 hours and preferably from about 24 hours to 180 hours. During this stage of pyrolyzation it is essential that the feedstock be in an essentially solid state with at most only incipient surface fusion of particles, as distinguished from the molten, i.e. liquid state so that substantial sublimation can occur as well as evolution of ammonium from the product.

A typical feedstock for this process may be prepared, for example, by reacting urea at 157° C. and 160 mm Hg for 3.5 hours to give a product having an analysis by weight of urea 37.5%, biuret 41.6% and cyanuric acid 16.1%, cooling the autoclave product below its melting point, and comminuting it. One method of accomplishing this is to drain the molten product into trays and allow it to cool naturally and solidify before comminuting, preferably with preformed biuret powder addition to provide crystallization "seed" and improve cooling rate.

It is advantageous in carrying out the process of the invention to have the feedstock comminuted to a mesh size of about 1 mesh and smaller (i.e. where the diameter of the particles is 1 inch and smaller, and preferably about 4 mesh and less.

The ground feedstock is suitably placed in trays or the like to a bed depth of between ½ inch and 3 feet or more, and placed in a forced air circulating oven or the like with hot air circulated through the particulate mass in each tray, preferably upwardly through each tray. The temperature is preferably thermostatically controlled to within ±3° C. within the oven.

The comminuted feedstock is placed in or on a container porous to air, such as a tray or other boxtype container with a screen or like foraminous bottom and open top, which arrangements provide what may be generically termed a fixed bed. Alternatively, the feedstock bed may be arranged on a wire screen or like foraminous conveyor, or in a fluidizing chamber, which arrangements provide what may be generically termed a movable bed.

The depth of the bed of the particulate material can be any desired depth consistent with the need to maintain substantial and continuing forced air flow in contact with the material surfaces, and considering also that under a given operating condition a given total amount of contact of moving air with the surfaces of the particles is necessary to achieve the result of substantial urea sublimation and urea conversion to biuret, which considerations involve several interrelated factors such as average mesh size of the particles, the temperature of the air, the depth of the particle bed and the volume of air flow past the particles. Thus, for example, in a situation where a fixed bed, two feet in depth, is composed of particles having an average mesh size of 8 mesh, a pressure drop of 0.16 psig per foot of bed has been found satisfactory for the operating condition where the air and particles are heated to a temperature of 127° C. and for 36 hours. Correspondingly, however, when the average particle size is 4 mesh, an optimized pressure drop through a bed 2 feet thick to accomplish a similar end product at the same temperature has been found to be 0.13 psig per foot of bed, and the heating should continue for a period of 50 hours.

Comminution of the solidified and broken up pieces of the partially pyrolyzed reaction product resulting from the first stage of reaction of urea and the addition thereto of feed grade biuret powder to increase the melting point and expedite cooling of the reaction product, can be carried out in any appropriate mechanical disintegrater such as a jaw crusher or rotary crusher, or hammermill or the like.

The powdered material added to expedite crystallization and cooling of the partially pyrolyzed reaction product to make the feedstock for the solid state heating stage of the process, other powdered or comminuted materials can be used as the additive if they do not substantially lower the melting point of the reaction mass during the solid state pyrolyzation and provided they are advantageous or at least not deleterious to the end use of the final reaction product, such as for animal feed or the like. In the case of the end use being animal feed, for example, advantageous additives may be calcium carbonate or calcium phosphate or other known animal feed additive.

However, the powdered or comminuted additive introduced to the partially pyrolyzed reaction product in making up the feedstock is preferably feed grade biuret such as readily available by-product fines from earlier sizing processing, and offers the advantage of increasing the melting point of the reaction mass during the solid state pyrolyzation (since the proportion of biuret and its homologs is thereby increased in the mass) which in turn permits it being heated during the solid state pyrolyzation to a somewhat higher temperature without melting, thus accelerating the heat conversion.

We have found that the two stage pyrolyzation technique described results in a product which when comminuted needs no further processing before use as animal feed grade biuret. In general, the initial stage of the reaction process is carried out at a temperature above the melting point of urea, forming a partially pyrolyzed reaction product comprising urea, cyanuric acid and biuret. The second stage of the process involves the continued pyrolyzation of the reaction product in particulate, essentially solid state, with forced hot air flow interstitially through the particles, the net effect of which is to reduce the urea content and enhance the biuret content of the reaction mass, while only slightly increasing the cyanuric acid, triuret and other by-product content. During the solid state heat treatment, some urea is sublimed as may also be a slight amount of biuret and possibly others. The effect of this sublimation in reducing the urea content of the product is substantial and is an important part of the process when one is attempting to produce FDA acceptable material having not more than 15% urea.

Investigation has revealed that carrying out the final pyrolysis reaction at a low temperature at or slightly below about the softening point of feed material retards the conversion of biuret into cyanuric acid, but permits effective further conversion of urea into biuret and the lowering of the urea content, and that such pyrolysis can be done with the reaction mass in a dry, particulate state.

When molten urea is heated first at atmospheric pressure and thereafter under vacuum, there is a rapid evolution of ammonia upon the application of the vacuum. This indicates the presence of a substantial quantity of biuret precursor moieties generated during the pyrolysis at atmospheric pressure. These active bodies then react under the influence of reduced pressure to give enhanced yields of biuret without excessive production of cyanuric acid.

It accordingly is evident that the pyrolytic conversion of urea to various products is highly sensitive to the reaction conditions of time, temperature and pressure. It is the essence of the first pyrolysis reaction that the conditions of high temperature pyrolysis at temperatures exceeding the melting point of urea are controlled and used for only a brief, first portion of our process in order to produce a feedstock for the second reaction which is controlled in composition; with the conversion of urea to biuret being then continued at a lower temperature with the reaction mass in the substantially solid state to react the feed.

Acceptable elevated temperature pyrolysis to prepare the partially reacted feedstock for the solid state pyrolyzation are the following, wherein the percentages are given in percent by weight:

| Constituent | General Limits | Optimum Limits |
|---|---|---|
| Cyanuric acid | 0–25% | 0–20% |
| Biuret | 20–60% | 35–60% |
| Urea | 20–60% | 20–45% |

In a manner known per se in the art, pyrolysis products having compositions within the foregoing ranges are obtainable, for example, by adjusting the pyrolysis variables of time, temperatures and pressure to within the following limits, with time and temperature being generally inversely related:

| Parameter | General Limits | Optimum Limits |
|---|---|---|
| Time (hours) | 0.25–24 | 1.0–4.0 |
| Temperature (°C.) | 200–135 | 175–135 |
| Pressure (mm) | 0–1520 | 0–200 |

A feed-grade biuret can readily be obtained by reacting the intermediate feedstock prepared in the above manner, with or without seed material addition during cooling, by adjusting the reaction variables of time, temperature and pressure to within the following limits, with time and temperature being generally inversely related:

| Parameter | General Limits | Optimum Limits |
|---|---|---|
| Time (hours) | 5–200 | 12–180 |
| Temperature (°C.) | 140–100 | 130–110 |
| Pressure (mm.Hg.ABS.) | 10–1520 | 50–760 |

The process may be carried out under atmospheric pressure or such slight negative pressure as may be required to recover the by-product ammonia. While higher pressure than atmospheric pressure may be used, there is no particular advantage in its use. Where the heat treatment is carried out under vacuum, it has been found that the reaction proceeds faster.

The foregoing parameters may be varied as desired so long as the second stage of the pyrolyzation reaction results in an acceptable level of the constituents in the final product, notably a high level of biuret and a cyanuric acid and urea concentration within the prescribed composition parameters as set forth below:

| Component | General Limits | Optimum Limits |
|---|---|---|
| Cyanuric acid | less than 50% | less than 30% |
| Biuret | 30–70% | 40–60% |
| Urea | less than 40% | less than 15% |

In a given run, when the feed material for the further pyrolyzation of the product in solid form is at hand and a determination is to be made as to the temperature at which the further, second stage pyrolyzation is to proceed, a sample of the feed material can be analyzed for softening point, such as by analysis on a Fisher Johns melting point detector, as marketed by the Fisher Scientific Company. During such an analysis, as the temperature of the sample is raised progressively, and as it reaches the point where the sample starts to soften, its color changes from a white dry, particulate appearance to a duller, greyish moist, shiny appearance. Further increase in temperature then causes such moist appearance to change to a glistening appearance and finally to a puddled, melted stage which is definitely a melting point. The temperature at which the first change in appearance from softening occurs is the temperature at or slightly below which the final pyrolyzation of the product should start. However, as the further pyrolyzation reaction proceeds, and the urea content of the reaction mass is further reduced with the biuret content thereof progressively increasing, the softening point of the mass will progressively increase somewhat because of the changing constituency of the reaction mass which progressive increase in softening point can permit a somewhat progressive increase in the temperature at which the reaction proceeds in the course of the run.

It has also been found that the feed material, being a mixture of several compounds, i.e. urea, biuret, cyanuric acid and other homologs, apparently demonstrates an eutectic action, i.e. the softening point is at a temperature somewhat less than the melting point of the urea and considerably less of course than the melting points of the other constituents, principally biuret and cyanuric acid. The melting point of urea itself is 132° C. but the initial softening point at least at the start of the second stage pyrolyzation oftentimes is somewhat less, e.g. 123° C., particularly in the instance where there has been no or minimal seed material addition of the type where the seed material has a relatively high biuret content and relatively low urea content as compared with the constituency of the intermediate reaction product obtained from the first stage pyrolyzation. Interestingly, the melting point of the final product, i.e. feed grade biuret, is at around 190° C. if in fact it even melts. The phenomenon involved apparently is that of disintegration of the biuret to cyanuric acid at the higher temperature.

The final reaction product is sized as in a hammermill to 16–20 mesh and fines resulting from the comminution which are considered too small for the final product can readily be recycled to the first phase reaction product as the seed material or part of the seed material added during cooling thereof.

BEST MODE OF CARRYING OUT THE INVENTION

EXAMPLE 1

A charge of commercially available technical grade urea was placed in an autoclave set at 157.2° C. ±2° C. The autoclave was evacuated to a pressure of 160 mm Hg Abs. The charge was held in the autoclave at the foregoing conditions for 3.5 hours. The intermediate product resulting from the initial autoclave reaction had the following composition:

| Constituent | % by Weight |
| --- | --- |
| Urea | 37.5 |
| Biuret | 41.6 |
| Cyanuric acid | 16.1 |
| Other Pyrolysis Products | 4.8 |
| | 100.0 |

A solid comminuted intermediate feedstock consisting of 591 grams of the above product was placed in an aluminum tray to a depth of 1.5 inches and given a heat treatment in a circulating oven at 112°–122° C. for 42 hours with forced air flow across the tray, during which time the material which had a size distribution of between four and twenty mesh was allowed to remain undisturbed. At the end of the heat treatment, the analysis of a uniform sample was: 14.3% urea, 60.0% biuret, 24.5 cyanuric acid, and 1.2% other related by-products.

During the 42 hour treatment at 112°–122° C., the urea content dropped from 37.5% urea to 14.3% urea. The biuret content increased from 41.6% biuret to 60.0% biuret, and the cyanuric acid increased from 16.1% to 24.5%. The gaseous ammonia given off during the oven treatment was checked and found to be stoichiometric with the formation of biuret and cyanuric acid.

EXAMPLE 2

A feedstock of 591 grams of a partially pyrolyzed urea product consisting of particles substantially ⅛" to ¼" in diameter and having an analysis of 38.4% urea, 42.8% biuret, and 14.1% cyanuric acid, formed by the feedstock preparation process described in Example 1, was placed in an aluminum tray to a depth of 1.5 inches and heated in a Farberware Turbo oven for 50 hours at 118°–122° C., with forced air flow across the tray. The material in the tray was turned over once every 10 hours to aid in uniformizing the reaction. At the conclusion of the heating period, the product analyzed 10.5% urea, 57.8% biuret, 19.4% of cyanuric acid, and 12.3% other urea pyrolysis products.

EXAMPLE 3

A feedstock comprising 591 grams of a partially pyrolyzed urea product prepared as in Example 1 and analyzing 37.5 urea and 16.1% cyanuric acid, was placed in an aluminum tray to a depth of 1.75 inches and heated in a Faberware Turbo oven for 33 hours total heating time, with forced air flow across the tray. At the end of the first 16 hours of heating, during which the oven temperature was between 116°–122° C., the product analyzed 29.0% urea, 46.7% biuret, 20.0% cyanuric acid and 3.3% others. The temperature of the oven was adjusted slightly upwards to 126°–130° C. for another 17 hours of heating, at the conclusion of which the product analyzed 16.8% urea, 31.9% biuret, and 42.5% cyanuric acid.

This exemplifies a mode of operation, i.e. a total 33 hours of heating between 116°–130° C., which produces a product higher in cyanuric acid and in urea than the current U.S. Food and Drug Administration specification for animal feed grade biuret but which has utility in other feed grades or for other purposes.

EXAMPLE 4

As a further example of practice of the present invention, on a larger scale and with greater efficiency in terms of volume of production of animal feed grade biuret, 900 pounds of urea was charged to a 100 gallon autoclave reactor, and melted by heating to a temperature of 149° C., with a partial pressure of 70 mm Hg applied to remove evolved ammonia. The molten urea was thus pyrolyzed for a period of four hours at a temperature ranging from 146° C. to 157° C. with the temperature in general progressively increasing during this period. At the end of the four hour period the molten crude partially pyrolyzed reaction product was discharged into a barrel trough equipped with an auger for stirring. At this point in the process the reaction product weighed about 750 pounds and was a white, creamy fluid material with an analysis as follows: urea 35%, biuret 48%, cyanuric acid 14%, others 3%, by weight, with a softening point of 123° C.

To prepare feedstock for the second stage of pyrolyzation of the molten crude reaction product from the foregoing reaction, while the mass was still fluid and being stirred by the auger, there was added thereto 83 pounds of a pre-formed powdered biuret reaction product from a previous process, analyzing 12% urea, 58% biuret, 20 cyanuric acid, and 10% related homologs, by weight. As will be noted, the amount of such pre-formed powdered biuret reaction product added was approximately 10% by weight of the molten crude product. It has been determined that the amount of this powder addition, when employed, should be from about 5% to about 25% relative to the weight of the molten crude reaction product, depending upon availability and need from the point of view of expediting the cooling of the crude product. In this instance, after the approximately 10% by weight powder addition, the resulting mixture analyzed as follows: 32.9% urea, 48.9% biuret, 14.5% cyanuric acid, and 3.6% other homologs, with a softening point of 135° C. As will be understood by those skilled in the art to which the invention is addressed, the proportionate reduction in urea content and slight increase in content of the other constituents also functions to raise the softening point of the mixture somewhat, which in turn permits a somewhat higher reaction temperature during the following stage of pyrolyzation, consistent with the requirement that the subsequent stage of pyrolyzation occur with the reaction mass in particulate, essentially solid state, i.e. at a temperature at or slightly below the softening point of the reaction mass.

Stirring of the crude intermediate reaction product with powdered feed grade biuret added, was continued, with the mixture becoming increasingly thicker and attaining a cookie-dough like character when the temperature reached about 110° C. At this point the auger was removed from the trough and material spread out on a cement floor and allowed to further cool. The material while still dough-like was cut and chopped into chunks with rakes and shovels and these discrete particles assumed a rigid character and became hard at about 90° C. Upon cooling of the particles to essentially room temperature, they were passed through a hammermill and comminuted to a particle size of 1 mesh and smaller (1 inch in diameter and smaller). Comminuted particles in the 1 mesh to 4 mesh range were then segregated and placed in a 4'×4' steel box with a fine mesh screen in the bottom and the box was placed in a circulating oven, with a product bed in the box having a depth of about 22 inches. Particles smaller than 4 mesh resulting from the comminution step were set aside for remelting in the crude reaction product of a subsequent batch, and may be conveniently added thereto at the same time as the feed grade biuret powder addition to the molten crude product.

The particulated reaction mass contained in the box was then heated by a duct heater and forced air flow upwardly through the box, to a temperature of 130° C., the air flow through the box being at about 6000 cubic feet per minute. Such heating and forced air flow was continued for a period of 24 hours, during which the reaction mask particles retained their shape but become slightly soft with some degree of surface fusion, which was easily broken by stirring with the particles retaining their discrete character. Heating was continued for a total period of 40 hours and at the end of this time the product, which continued to be essentially free flowing irregular particles, was removed from the oven and emptied from the steel box, and analyzed 14% urea, 58% biuret, 17% cyanuric acid and 11% other homologs. Upon cooling the reaction product was comminuted to powder form, in a hammermill, to a particle size of 16–20 mesh, and was deemed suitable for use as feed grade biuret without further treatment.

EXAMPLE 5

600 pounds of urea was charged to a 100 gallon reactor equipped with a 36 KW heater. The charge was heated to a temperature of 152° C. and the molten reaction mass held at this temperature for a period of 4.5 hours, during which time evolved ammonia gas was removed by air bubbled out through the mass at the rate of 175 cubic feet per minute. At the end of the 4.5 hour pyrolyzation period, 520 pounds of molten pyrolysis product were recovered from the reactor, analyzing 33.7% urea, 14.8% cyanuric acid, 46.4% biuret and 5.1% other homologs, with a softening point of 128° C. The temperature of the molten product as recovered from the reactor was 149° C. While stirring the product with a ribbon auger in an open barrel trough, 60 pounds of feed grade biuret powder at 13° C. and analyzing 12% urea, 18.8% cyanuric acid, 63.3% biuret, and 5.9% other homologs were blended into the molten mass. An additional 123 pounds of powdered material analyzing 34.5% urea, 12.9% cyanuric acid, 47.9% biuret, and 5.5% other homologs (and obtained as fines resulting from the comminution of the partially pyrolyzed reaction product from a previous run) was also added to the molten mass. These powder additions brought the temperature of the whole mixture down to 115° C., at which point the mixture had a very thick dough-like consistency. This material was next allowed to cool to about 72° C. at which point it was run through a hammermill and ground to 1 mesh to 4 mesh particle size. The mixing, cooling and grinding required a total of 45 minutes time. It is notable in this respect that, without addition of powdered seed material in the form of feed grade biuret powder and/or fines from a previous comminution of partially pyrolyzed reaction product, it can take as much as 16 hours for the molten partially pyrolyzed reaction product as discharged from the autoclave reactor to cool to the point where it is solidified and may be comminuted. It is thus apparent that the powdered material addition acts as seed material or what may be termed crystallization centers to materially improve the solidification rate of the product and to provide a more crystalline product, in contrast to the nature of the cooled product without any seed material addition, which is more amorphous and gummy in character.

600 pounds of the comminuted feedstock material of 1 mesh to 4 mesh size was placed in a 4'×4' steel box with a screen bottom and the box containing this bed of product, with a bed thickness of 11 inches, was placed in a recirculating oven and heated to a temperature of 130° C. by forced air recirculation upwardly through the bed at a rate of 6000 cubic feet per minute. After 24 hours of such recirculation of the heated air, the particles were slightly fused together and were manually broken apart by stirring with a shovel. Heating was then continued by further forced air recirculation at the same temperature for a total period of 40 hours, during which time some 28 pounds of ammonia and some 22 pounds of sublimate evolved. The final product, still in discrete particle form with only slight, readily broken surface fusion of the particles, analyzed 14.3% urea, 17.6% cyanuric acid, 62.7% biuret and 5.4% other homologs.

EXAMPLE 6

900 pounds of urea was charged to a 100 gallon reactor equipped with a 36 KW heater and melted and heated to a temperature of 152° C. for 2½ hours, with a partial pressure of 70 mm Hg being maintained, the evolved ammonia being captured in a water trap. Heating was continued for an additional 4 hours. During this time 110 pounds of ammonia was released and 30 pounds of the reaction mass was lost as sublimate. 760 pounds of molten reaction product was recovered from the reactor, and analyzed 34.2% urea, 12.3% cyanuric acid, 51.5% biuret, and 2% other homologs, with a softening point of 127° C. To this product was added 70 pounds of feed grade biuret analyzing 12.0% urea, 18.8% cyanuric acid, 63.3% biuret, and 5.9% other homologs, and the mixture when cooled was comminuted to particles of 1 mesh size and less, as in Example 1. This comminuted feedstock and some additional feedstock from a previous batch, making up a feedstock mix weighing 1281.5 pounds with a softening point of 141° C., was loaded into the box and oven described in Example 5, the depth of the material bed after such loading being 22 inches. Heated air was then blown through the bed by an upward recirculation by means of a 6000 cubic feet per minute blower, with the air maintained at a temperature of 132° C. for a total heating time in the oven of 56.75 hours, and the resulting product yield weighed 1079 pounds and analyzed 17.1% urea, 17.6% cyanuric acid, 54.1 biuret, and 11.2 other homologs. In this instance the particulate product bed in the box was not disturbed for the entire period of heating. Although in this instance the urea content of the final reaction product is somewhat high and the biuret content slightly lower than specification requirements for feed grade biuret, it will be recognized that such a product can be mixed with other reaction products such as that resulting in Example 4 or Example 5 to provide a product mix which meets feed grade specifications, if desired.

EXAMPLE 7

Feedstock for solid state pyrolyzation according to the present invention was prepared as in Example 6 but without any feed grade biuret powder addition. This feedstock was comminuted to an average particle size of 4 mesh and analyzed 37.1% urea, 12.9% cyanuric acid, 47.8% biuret, and 2.2% other homologs, with a softening point of 123° C. The feedstock was placed in the 4'×4' steel box with bottom screen and in the oven for forced air recirculation as in Example 4 and the material was heated by the recirculating forced air at a volume of 6000 cubic feet per minute and at a temperature of 132° C. In 24 hours the product had fused into a solid mass so that most of the particle distinction had been lost and it was evident that ammonia had been entrapped in the xass in the press, since the blower was not able to drive air through the mass at this point and the material after such heating analyzed 31.1% urea, 14.1% cyanuric acid, 50.2% biuret and 4.6% other homologs.

EXAMPLE 8

A further quantity of the same feedstock as in Example 6 was arranged in a bed of 11 inches depth in the same steel box and heated in the oven by recirculating air as in Example 6 but with the temperature of the recirculating air maintained at 121° C., for a period of 72 hours. During this heating the product in the bed remained in discrete particles, ammonia by-product evolved in the approximate amount of 28 pounds, and the final reaction product on cooling and recomminution analyzed 13.0% urea, 15.1% cyanuric acid, 59.4 biuret, and 12.5% other homologs.

It will be understood that the foregoing examples are merely illustrative of the invention and that variations will readily occur to those skilled in the art to which the invention is addressed as to the equipment and processing conditions under which pyrolysis reactions characteristic of the present invention proceed, within the scope of the following claims.

What is claimed is:

1. A process in which urea is pyrolytically converted to biuret, said process comprising heating, in dry, particulate, and essentially solid state, a partially pyrolyzed reaction product containing from about 20% to about 60% urea and not more than about 25% cyantric acid by weight, the heating of such feedstock occurring at a temperature substantially at or slightly below the softening temperature of the particles with forced hot air flow interstitially through the particles for a sufficient time to lower the urea content thereof, partly by partial sublimation of the urea and partly by further reaction thereof to biuret.

2. The process of claim 1, comprising heating the particles at a temperature of between about 100° C. to about 140° C.

3. The process of claim 1, comprising heating the particles at a temperature of from about 110° C. to about 130°.

4. The process of claim 1, comprising heating the particulate reaction product with forced air circulation therethrough for a time sufficient to reduce the urea content thereof to less than about 15% by weight.

5. The process of claim 1 or claim 4, wherein the partially pyrolyzed reaction product comprising the feed-stock for the process is prepared by subjecting urea to a pyrolyzation for a time and temperature, in generally inverse relation, of between about 15 minutes at about 200° C. and about 10 hours at about 135° C., followed by cooling of the resulting partially pyrolyzed reaction product to solid form, and by comminuting same.

6. The process of claim 5, comprising promoting crystallization and accelerating cooling of the partially pyrolyzed reaction product by adding thereto a seed material in powder form.

7. The process of claim 5, comprising adding to the partially pyrolyzed reaction product, to increase the softening point thereof when used as a particulate feedstock for further pyrolyzation in solid state, a material substantially lower in urea content and substantially higher in biuret content than are contained in the reaction product.

8. The process of claim 5, further comprising adding to the partially pyrolyzed reaction product in molten form, and in an amount at least about 5% of the weight thereof, one or more powdered materials selected from the group consisting of animal feed grade biuren recognized animal feed supplements, and mixtures thereof.

9. The process of claim 5, wherein cooling of a partially pyrolyzed reaction product to form the feedstock is accelerated by adding to the molten reaction product previously prepared feed grade biuret in powder form, and agitating the mixture during cooling thereof.

10. The process of claim 9, wherein the powdered feed grade biuret is added to the reaction product in an amount equal to about 5% to about 25% by weight relative to the weight of the reaction product.

11. The process of claim 10, wherein the added powder is added in an amount equal to about 10% by weight relative to the weight of the partially pyrolyzed reaction product.

12. The process according to claim 9, comprising also adding to the partially pyrolyzed reaction product in molten form, powdered material obtained as fines in the course of the comminution of previously partially pyrolyzed reaction product from an earlier run.

13. The process of claim 4, wherein the particle size of the feedstock is about 1 mesh or less.

14. The process of claim 4, wherein the particle size of the feedstock is in the range of about 4 mesh to about 16 mesh.

15. The process according to claim 4, comprising arranging the particulate feedstock in a bed to a depth of up to about three feet, and causing forced air circulation vertically therethrough.

16. The process according to claim 15, wherein the heating of the bed of particulate feedstock is by passing heated forced air upwardly therethrough.

17. The process according to claim 4, comprising arranging the particulate feedstock in a bed to a depth of less than about 5 inches, and causing forced air circulation generally horizontally across the bed.

* * * * *